(12) United States Patent
Johnson et al.

(10) Patent No.: US 11,426,600 B2
(45) Date of Patent: *Aug. 30, 2022

(54) PHOTOBIOMODULATION THERAPY TO DELAY DYSTROPHY PROGRESSION

(71) Applicant: Multi Radiance Medical, Solon, OH (US)

(72) Inventors: Douglas Johnson, Brownstown, MI (US); Max Kanarsky, Solon, OH (US); Ernesto Leal-Junior, Sao Paulo (BR)

(73) Assignee: MULTI RADIANCE MEDICAL, Solon, OH (US)

( * ) Notice: Subject to any disclaimer, the term of this patent is extended or adjusted under 35 U.S.C. 154(b) by 357 days.

This patent is subject to a terminal disclaimer.

(21) Appl. No.: 16/604,752

(22) PCT Filed: Apr. 13, 2018

(86) PCT No.: PCT/US2018/027517
§ 371 (c)(1),
(2) Date: Oct. 11, 2019

(87) PCT Pub. No.: WO2018/191637
PCT Pub. Date: Oct. 18, 2018

(65) Prior Publication Data
US 2020/0376291 A1 Dec. 3, 2020

Related U.S. Application Data

(60) Provisional application No. 62/485,071, filed on Apr. 13, 2017.

(51) Int. Cl.
*A61N 5/06* (2006.01)
*A61N 2/00* (2006.01)

(52) U.S. Cl.
CPC .......... *A61N 5/0613* (2013.01); *A61N 2/002* (2013.01); *A61N 2/004* (2013.01); *A61N 2005/0615* (2013.01); *A61N 2005/0659* (2013.01)

(58) Field of Classification Search
CPC ...... A61N 5/0613; A61N 2/002; A61N 2/004; A61N 2005/0615; A61N 2005/0658; A61N 2005/0659
See application file for complete search history.

(56) References Cited

U.S. PATENT DOCUMENTS 10,744,337 B2 * 8/2020 Johnson .................. A61N 2/06
11,179,573 B2 * 11/2021 Johnson ............... A61N 5/0622
(Continued)

OTHER PUBLICATIONS

Antonialli, Fernanda Colella, et al. "Phototherapy in skeletal muscle performance and recovery after exercise: effect of combination of super-pulsed laser and light-emitting diodes." Lasers in medical science 29.6 (2014): 1967-1976.
(Continued)

*Primary Examiner* — Eric D. Bertram
*Assistant Examiner* — Michael T. Holtzclaw
(74) *Attorney, Agent, or Firm* — Tarolli, Sundheim, Covell & Tummino LLP

(57) ABSTRACT

Photobiomodulation therapy (PBMT) can be applied to a dystrophic muscle to delay dystrophy progression. A light source device can be contacted to a subject's skin proximal to a dystrophic muscle or muscle group. A light signal (with wavelengths from the red to infrared part of the spectrum) can be applied in at least one of a pulsed operating mode, a continuous operating mode, and a super-pulsed operating mode through the light source device to the dystrophic muscle or muscle group. The light signal is applied for a time sufficient to stimulate a phototherapeutic response in the dystrophic muscle or muscle group.

14 Claims, 18 Drawing Sheets

(56) References Cited

U.S. PATENT DOCUMENTS

| | | |
|---|---|---|
| 2004/0153130 A1 | 8/2004 | Oron |
| 2007/0129776 A1* | 6/2007 | Robins ................ A61N 5/0613 607/88 |
| 2009/0254154 A1* | 10/2009 | De Taboada ......... A61N 5/0613 607/88 |
| 2013/0066395 A1* | 3/2013 | Simon ................ A61B 5/4094 607/48 |
| 2014/0184089 A1 | 7/2014 | Porter |
| 2016/0220834 A1* | 8/2016 | Schwarz ................ A61N 1/40 |
| 2017/0072210 A1* | 3/2017 | Gangwish ................ A61N 7/00 |
| 2017/0128736 A1 | 5/2017 | Johnson et al. |
| 2022/0001194 A1* | 1/2022 | Johnson ................ A61N 5/067 |

OTHER PUBLICATIONS

Öztekin, ilhan, et al. "Therapeutic effects of Oligonol, acupuncture, and quantum light therapy in chronic nonbacterial prostatitis." Evidence-Based Complementary and Alternative Medicine 2015 (2015).

Dos Santos Grandinétti, Vanessa, et al. "The thermal impact of phototherapy with concurrent super-pulsed lasers and red and infrared LEDs on human skin." Lasers in medical science 30.5 (2015): 1575-1581.

Leal-Junior, Ernesto Cesar Pinto, et al. "Adjunctive use of combination of super-pulsed laser and light-emitting diodes phototherapy on nonspecific knee pain: double-blinded randomized placebo-controlled trial." Lasers in medical science 29.6 (2014): 1839-1847.

International Search Report dated Aug. 1, 2018 for International Application No. PCT/US18/27517.

* cited by examiner

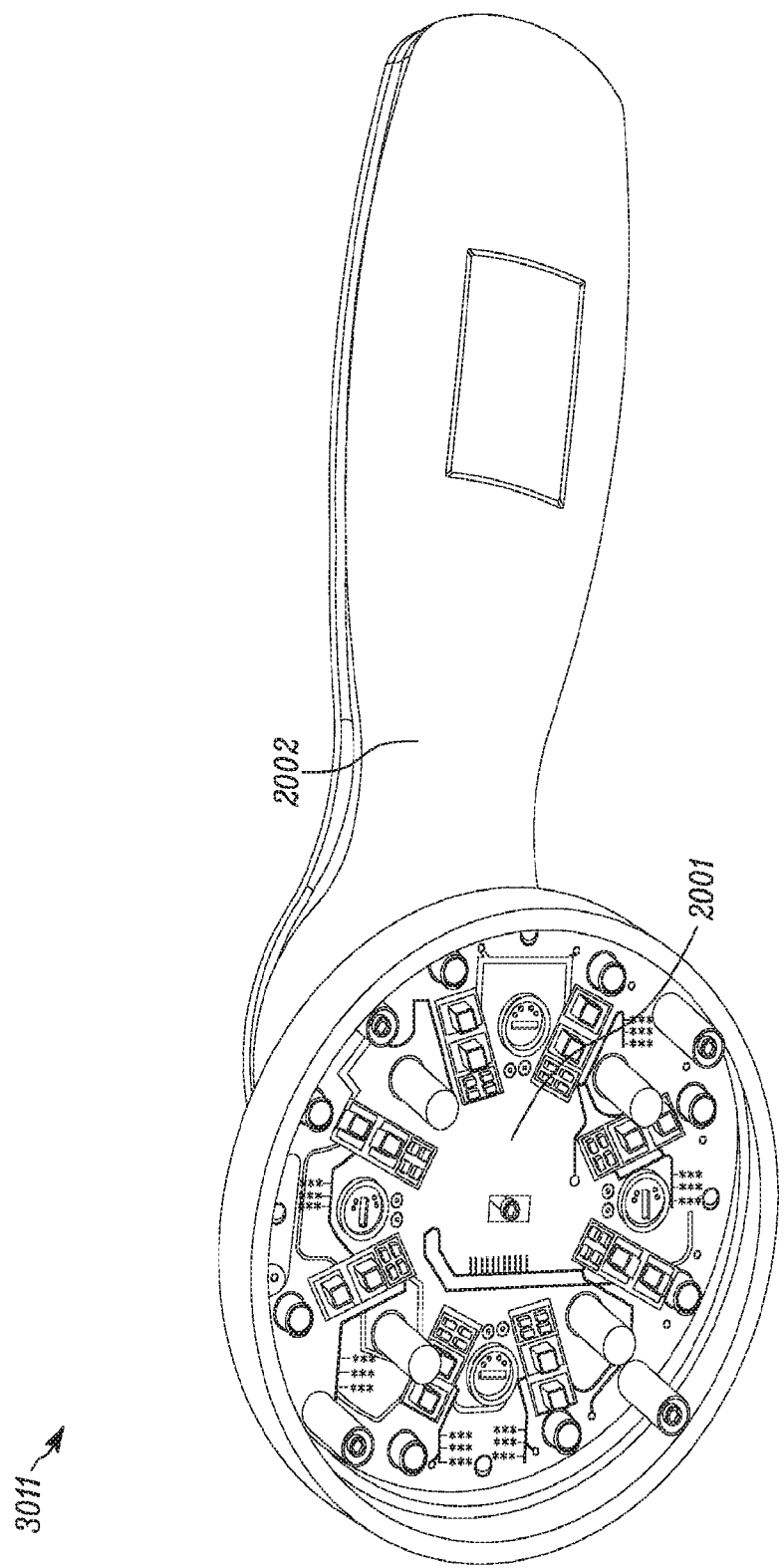

1

PHOTOBIOMODULATION THERAPY TO DELAY DYSTROPHY PROGRESSION

CROSS-REFERENCE TO RELATED APPLICATIONS

This application claims the benefit of U.S. Provisional Application No. 62/485,071, filed Apr. 13, 2017, entitled "SYSTEM OF USE OF LASERS AND/OR LEDS AND METHOD FOR THE REDUCTION OF MUSCLE ATROPHY, IMPROVEMENT IN FUNCTIONAL ADLs, PRESERVATION OF MUSCLE STRENGTH, AND INCREASE PROTEIN EXPRESSION OF DYTROPHIN IN SKELETAL MUSCLES ASSOCIATED WITH DUCHENNE'S MUSCUCLAR DYSTROPHY". This provisional application is hereby incorporated by reference in its entirety for all purposes.

TECHNICAL FIELD

The present disclosure relates generally to photobiomodulation therapy (PBMT) and, more specifically, to systems and methods that apply PBMT to a dystrophic muscle or muscle group to delay dystrophy progression.

BACKGROUND

Muscular dystrophy is a collection of inherited diseases, which are characterized by skeletal muscle weakness and degeneration. Duchene muscular dystrophy (DMD), one of the most common forms of muscular dystrophy, affects 1 in 3,500 newborn males worldwide. DMD is an X-linked recessive genetic disorder associated with mutations in the dystrophin gene, resulting in reduced expression of the protein dystrophin. Dystrophin serves as the intracellular link of the dystrophin-glycoprotein complex (or "dystrophin complex"), which is present in the sarcolemma of skeletal muscle. An important function of the dystrophin complex is the mechanical stabilization of stresses during eccentric muscle contraction. In addition, recent evidence suggests that dystrophin also plays an important role in the regulation of signaling pathways, particularly those that activate the production of reactive oxygen species (ROS), such as nitric oxide, and those that trigger the entry of calcium. Traditionally, DMD has been treated by the administration of corticoids. However, corticosteroids cannot be used as a long-term treatment. Accordingly, there is a need for a non-pharmacological treatment for DMD.

SUMMARY

The present disclosure relates generally to photobiomodulation therapy (PBMT) and, more specifically, to systems and methods that apply PBMT to a dystrophic muscle or muscle group to delay dystrophy progression. PBMT provides a non-pharmacological treatment for dystrophies, including Duchene muscular dystrophy (DMD), that can be used alone or in combination with a pharmaceutical therapy that is less damaging than traditional corticosteroids (e.g., a non-steroidal anti-inflammatory drug (NSAID)) and/or at a lower dose than traditional treatment by corticosteroids, enabling longer use of corticosteroids.

In one aspect, the present disclosure can include a method for applying PBMT to a patient diagnosed with muscular dystrophy to delay dystrophy progression. A light source device can be contacted to a subject's skin proximal to a dystrophic muscle or muscle group. A light signal can be applied in at least one of a pulsed operating mode, a continuous operating mode, and a super-pulsed operating mode through the light source device to the dystrophic muscle or muscle group. The light signal is applied for a time sufficient to stimulate a phototherapeutic response in the dystrophic muscle or muscle group.

In another aspect, the present disclosure can include a light source device to applying PBMT to a patient diagnosed with muscular dystrophy to delay dystrophy progression. The light source device can be configured to contact a subject's skin proximal to a dystrophic muscle or muscle group and includes a cluster of light delivery sources, a permanent magnet, a processing unit, and a power source. The cluster of light delivery sources can include: a first light source configured to generate a first portion of a light signal with a wavelength from 890-910 nm in a super-pulsed operating mode; a second light source configured to generate a second portion of the light signal with a wavelength from 600-700 nm in a pulsed operating mode or a continuous operating mode; and a third light source configured to generate a third portion of the light signal with a wavelength from 810-880 in the pulsed operating mode or the continuous operating mode. The permanent magnet can provide a constant magnetic field from 5 mT to 1 T. The processing unit can be preprogrammed with a time for application of the light signal to the dystrophic muscle or muscle group.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 23 shows a picture of another example of the light source device of FIG. 1.

DETAILED DESCRIPTION

I. Definitions

Figure 1:
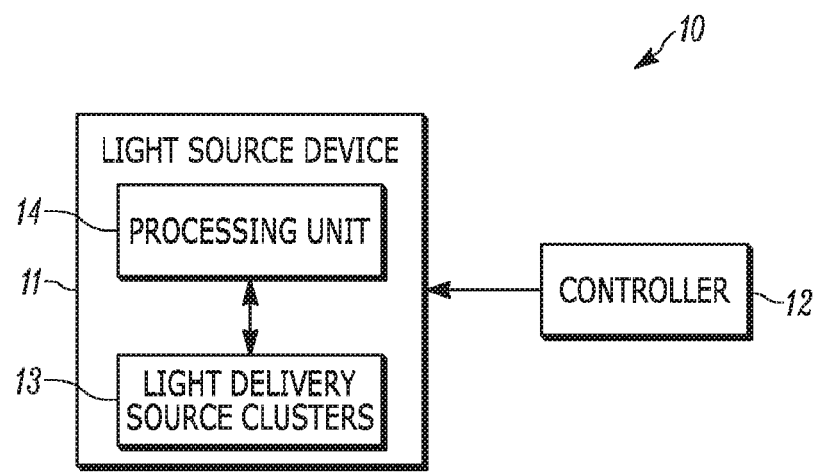
FIG. 1 is a block diagram illustration showing an example of a system that configures and applies a photobiomodulation therapy (PBMT) to a dystrophic muscle or muscle group to delay dystrophy progression in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the terms "comprises" and/or "comprising" can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "photobiomodulation" refers to the application of a light signal to a portion of a subject's body to induce a phototherapeutic response in cells within the portion of the subject's body.

As used herein, the term "photobiomodulation therapy (PBMT)" refers to a drug-free, non-invasive treatment procedure, in which a light signal is applied to a certain region of a subject's body to treat a certain medical condition (e.g., pain, injury, disorder, disease, or the like) via a phototherapeutic response. In some instances, PBMT can be used alone to induce a phototherapeutic response, but in other instances, PBMT can be used in combination with a pharmaceutical therapy that is less damaging than traditional corticosteroids (e.g., a non-steroidal anti-inflammatory drug (NSAID)) and/or at a lower dose than traditional treatment by corticosteroids, enabling longer use of corticosteroids As used herein, the term "light signal" refers to a combination of lights having wavelengths that create a synergistic effect when combined and improves the percentage of available light at greater tissue depths. In some instances, the wavelengths can be within a wavelength range of 600-1100 nm. For example, the wavelengths can include at least one wavelength corresponding to the visible range of the electromagnetic spectrum (e.g., red light) and at least one wavelength corresponding to the near-infrared or infrared range of the electromagnetic spectrum.

As used herein, the term "light source device" refers to a mechanical implement that can deliver a light signal of PMBT to a portion of the subject's body. Examples of the light source device include a probe, a flexible array device, or the like.

As used herein, the term "light source" refers to a component of a light source device that delivers one or more lights of different wavelengths. For example, the light source can be a low-level laser source (e.g., a laser light emitting diode (LED)) that generates coherent light. The low-level laser source can operate in a super pulsed mode that generates ultrashort pulses with a high peak power and minimal heat. As another example, the light source can be an incoherent light source, such as a traditional LED or light bulb. The incoherent light source can operate in a pulsed mode and/or a continuous mode.

As used herein, the term "phototherapeutic response" refers to a biological reaction to application of PBMT to a portion of the subject's body. For example, the light signal can be applied to a dystrophic muscle or muscle group to modulate gene and/or protein expression of dystrophin, and the phototherapeutic response can be increasing the expression of dystrophin in these dystrophic muscles or muscle groups, preserving the morphology of these dystrophic muscles or muscle groups, and/or improving muscle function in these dystrophic muscles or muscle groups.

As used herein, the term "dystrophy" refers to a medical condition in which an organ or tissue of a subject's body wastes away.

As used herein, the term "muscular dystrophy" refers to a hereditary condition due to mutations in one or more genes that are involved in making skeletal muscle protein. Muscular dystrophy is marked by progressive breakdown/weakening of muscles and/or loss of muscle mass. A muscle or muscle group that is "dystrophic" is a muscle or muscle group afflicted with muscular dystrophy. The most common type of muscular dystrophy is Duchenne muscular dystrophy (DMD); other types of muscular dystrophy include, but are not limited to, Becher muscular dystrophy, facioscapulohumeral muscular dystrophy, and myotonic dystrophy.

As used herein, the term "muscle" refers to skeletal muscle.

As used herein, the term "dystrophin" refers to a protein that is associated with a transmembrane complex of skeletal muscle fibers. Dystrophin can stabilize muscle fibers by forming a link between an internal cytoskeleton and a protein complex in a plasma membrane that is connected to an extracellular matrix.

As used herein, the term "progression" refers to a change in the way a medical condition affects a subject as it moves from its earliest stages to its peak and then its resolution.

As used herein, the term "proximal" refers to a location that is near a target. For example, a device that is located proximal a muscle or muscle group can be located over the muscle or muscle group, but need not be directly over the center of the muscle or the muscle group.

As used herein, the term "sufficient" refers to an amount adequate enough to satisfy a condition. For example, "a time sufficient to stimulate a photherapeutic response in dystrophic muscle or muscle group" can refer to a light signal being applied to a dystrophic muscle or muscle group for a time adequate enough to stimulate the photherapeutic response.

As used herein, the term "direct" refers to the absence of intervening elements. For example, a device that directly contacts a skin surface has no intervening elements between the device and the skin surface. When the term "contact" is used herein, it means "direct contact" unless otherwise stated.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to photobiomodulation therapy (PBMT) and, more specifically, to systems and methods that apply PBMT to a dystrophic muscle or muscle group to delay dystrophy progression. PBMT provides a non-pharmacological therapy to patients suffering from dystrophy, including muscular dystrophy. The PBMT can be used alone or in combination with a pharmaceutical treatment (either steroidal or non-steroidal) to manage the symptoms of muscular dystrophy.

Muscular dystrophy is characterized by skeletal muscle weakness and degeneration. By applying PBMT to a dystrophic muscle or muscle group in a transcutaneous and non-invasive manner, the PBMT can counteract the weakness and degeneration and lead to an improvement in function and overall quality of life. For example, Duchene muscular dystrophy (DMD) is a common form of muscular dystrophy associated with mutations in the dystrophin gene, which results in reduced expression of the protein dystrophin, which provides mechanical stabilization of stresses during eccentric muscle contraction and regulates signaling pathways. The PBMT can modulate gene and/or protein expression of dystrophin, increasing the expression of dystrophin in these dystrophic muscles or muscle groups. Accordingly, PBMT can provide the protective effects of delaying dystrophin loss, preserving muscle morphology, and improving muscle function.

III. Photobiomodulation Therapy (PBMT)

PBMT provides a non-pharmacological therapy that can be administered to a patient in a non-invasive manner to stimulate a photherapeutic response. As used herein, a light signal is applied through the skin of a patient suffering from dystrophy, including muscular dystrophy, to a dystrophic muscle or muscle group to stimulate a photherapeutic response. In this case, the photherapeutic response can include modulating gene and/or protein expression of dystrophin to preserve muscle morphology and improve muscular function. Inflammatory and immune responses play a key role in the pathogenesis of muscular dystrophy. PBMT works to counteract these inflammatory and immune responses to slow the progress of muscular dystrophy.

While not wishing to be bound by theory, there is strong evidence to suggest that one of the basic mechanisms of PBMT is the acceleration of electron transfer by electromagnetic radiation in the visible and near infrared region of the spectrum, via the modulation of cytochrome c-oxidase (CCO) activity. Traditionally, PBMT has attempted to modulate CCO activity using a single wavelength in the visible and near infrared region of the spectrum. However, the use of such single wavelengths cannot effectively modulate CCO activity since the single wavelength is limited by its specific absorption spectrum. The light signal used herein has a combination of wavelengths, which are used concurrently, providing an overlapping effect of peak activation, which accelerates CCO activity. Additionally, the time of CCO activation is prolonged across the entire therapeutic window by delivering much smaller doses across many wavelengths, rather than a single wavelength of a greater power. The multiple wavelengths enhance adenosine triphosphate (ATP) production, requiring less energy, and provides continual photodissociation of nitric oxide (NO), not only from CCO, but also from intracellular stores like nitrosylated forms of hemoglobin and myoglobin. NO is a potent vasodilator and PBMT can increase the vasodilation due to NO and increases the availability of oxygen to treated cells, and allows for greater traffic of immune cells into tissue, which counteracts inflammatory and immune responses and shows the progress of muscular dystrophy.

Accordingly, the light signal of the present disclosure includes a combination of individual light waves. The combination enhances each individual wavelength's ability to penetrate the skin, to allow for a greater portion of the available light energy to reach biological targets beneath the surface. Accordingly, the light signal can be configured so that individual light waves (from chosen light sources, with a selected wavelength, with a given power, and the like) within the light signal work constructively to create a synergistic effect. The light signal can be delivered by a light source device that includes a combination of one or more super pulsed lasers (which deliver a desired peak power from an ultrashort pulse with a minimized level of heat accumulated in the patient's tissue), one or more infrared emitting diodes, and one or more light emitting diodes. In some instances, the light source device can include groups of a super pulsed laser, an infrared emitting diode, and a light emitting diode. In other instances, the light source device can include groups of a super pulsed laser, at least three infrared emitting diodes, and at least three light source devices. The use of a super pulsed source can minimize the photo-thermal effect accumulating within the skin surface and target tissue. Additionally, the light source device can include a permanent magnet to provide a static (or constant) magnetic field.

IV. Systems

One aspect of the present disclosure can include a system 10 (FIG. 1) that applies photobiomodulation therapy (PBMT) to a dystrophic muscle or muscle group in a subject who has been diagnosed with a type of dystrophy, like muscular dystrophy. In response to the PBMT, the dystrophic muscle or muscle group can undergo a phototherapeutic response, which can delay dystrophy progression or otherwise treat dystrophy. For example, a subject can be diagnosed with a form of muscular dystrophy, like Duchene muscular dystrophy (DMD), which is characterized by skeletal muscle weakness and degeneration. The phototherapeutic response can counteract the weakness and degeneration characteristic of muscular dystrophy and lead to an improvement in function and overall quality of life. DMD, in particular, is associated with mutations in the dystrophin gene, which results in reduced expression of the protein dystrophin. Through the phototherapeutic response, the PBMT can modulate gene and/or protein expression of dystrophin, increasing the expression of dystrophin in the dystrophic muscle or muscle group. Accordingly, the PBMT of the system 10 can provide the protective phototherapeutic effects of delaying dystrophin loss, preserving muscle morphology, and improving muscle function. While PBMT is a non-pharmacological therapy that can be used alone to treat dystrophy, PBMT can also be used in combination with a pharmaceutical treatment (either steroidal or non-steroidal) to treat dystrophy.

The system 10 can include at least a light source device 11 that delivers the PBMT to the dystrophic muscle or muscle group and a controller 12 to deliver inputs to the light source device 11 related to the delivery of the PBMT via a wired connection and/or a wireless connection. The PBMT can be applied to the dystrophic muscle or muscle group by a light signal that is generated by a light source device 11. To facilitate the delivery of the light signal to the diastrophic muscle or muscle group, the light source device 11 can be shaped so that at least a portion makes contact with the subject's skin proximal to the dystrophic muscle or muscle group.

Figure 20:
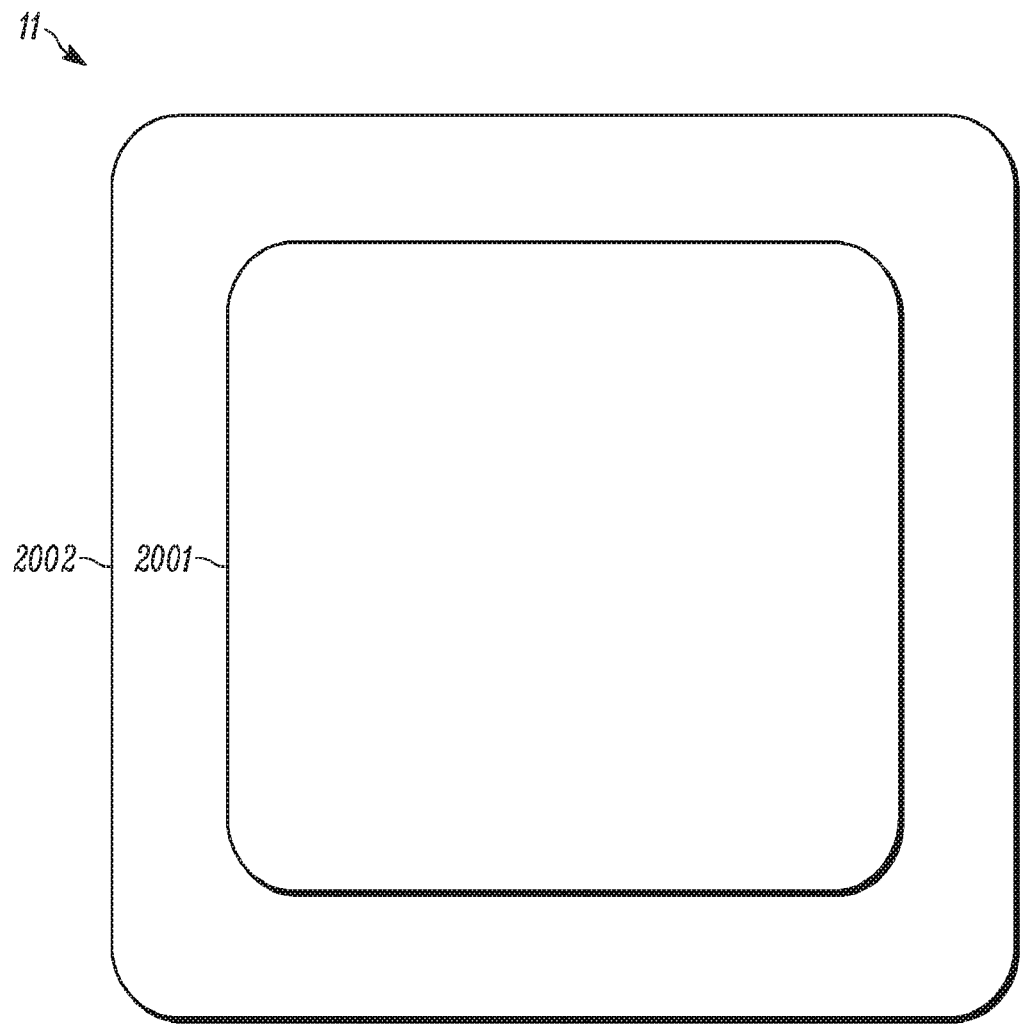
FIG. 20 shows a diagram of an example of the light source device of FIG. 1.

The light source device 11 can be configured in any shape that facilitates contacting a portion of the skin and/or the delivery of the light signal. An example of the light source device 11, including an electronics housing 2001 and a device housing 2002, is shown in FIG. 20. The electronics housing 2001 can include processing unit 14 and the power source and other electronics required for operation of the light source device 11. The device housing 2002 can surround the electronics housing and stabilize the electronics housing 2001. In some instances, the device housing 2002 can embody a securing mechanism to removeably secure the light source device 11 to an area of the subject's skin. For example, the securing mechanism can be able to be disconnected to facilitate movement of the light source device 11. Even in the absence of the securing mechanism, the light source device 11 can be portable with at least a portion being able to be moved to different areas of the subject's body. The attachment mechanism. Light delivery source clusters 13 can be within the electronics housing 2001 and/or within the device housing 2002.

Figure 21:
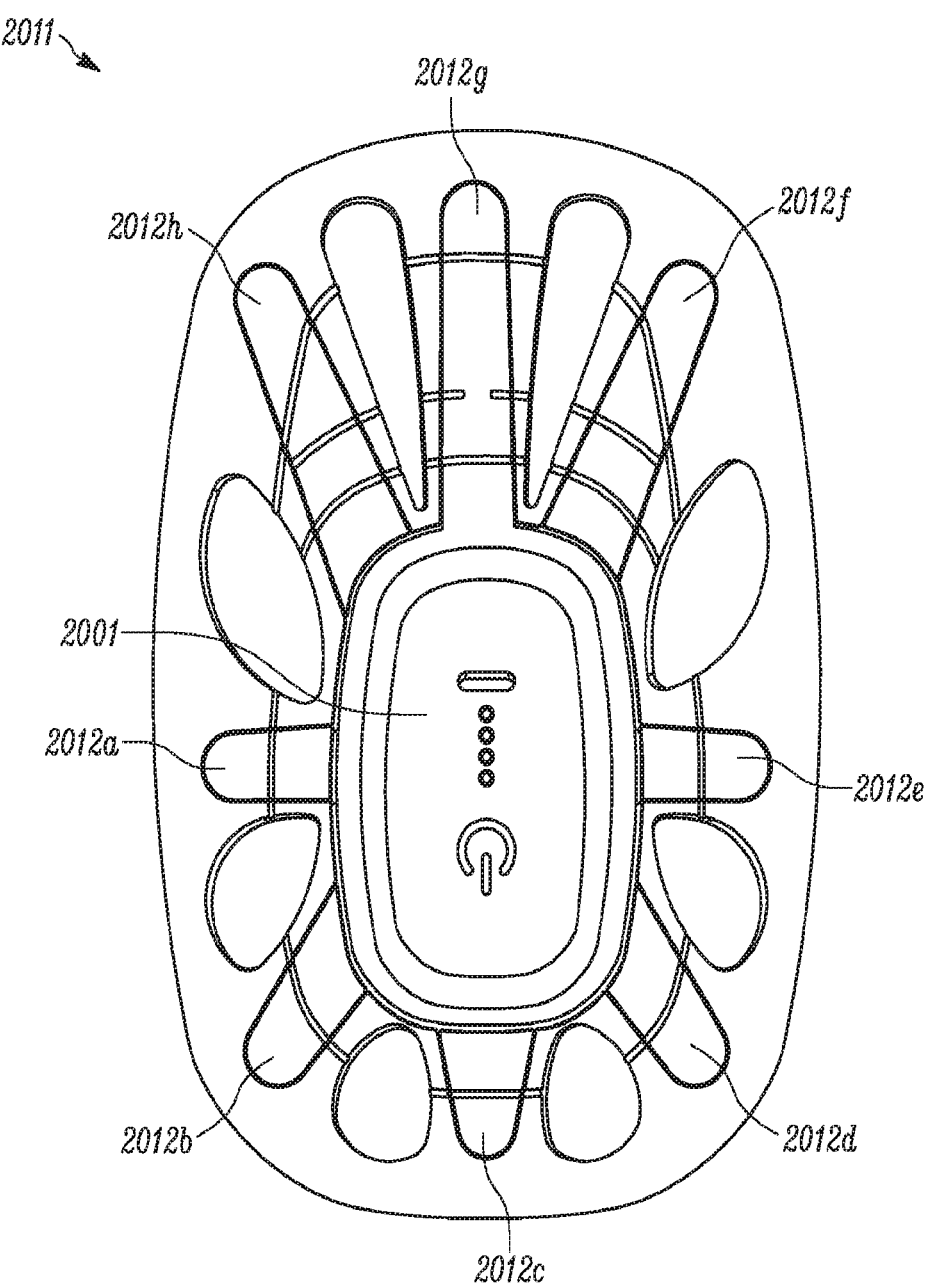
FIG. 21 shows a picture of another example of the light source device of FIG. 1.
Figure 22:
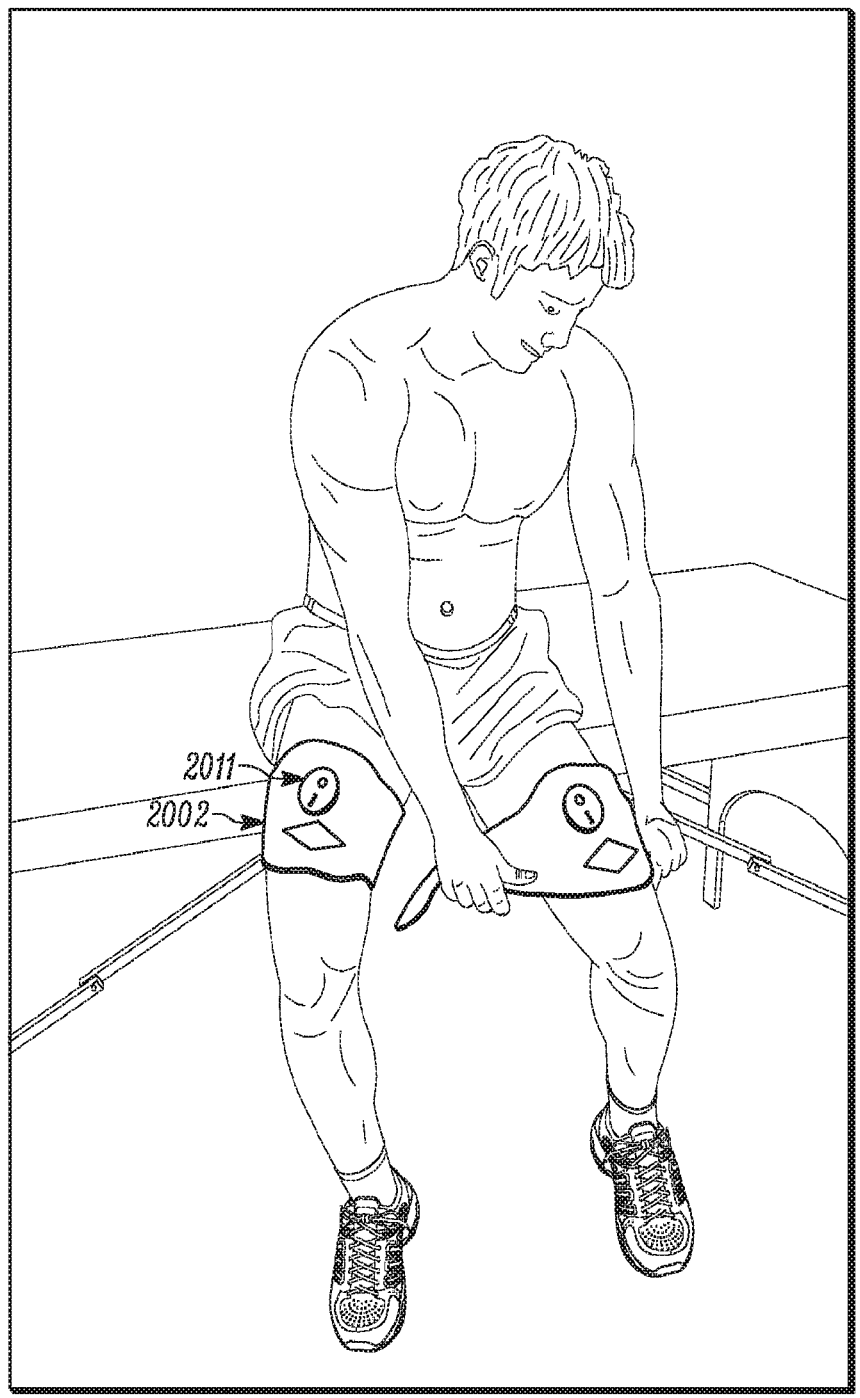
FIG. 22 shows a picture of an example use of the light source device shown in FIG. 21.

As one example, the light source device 11 can be embodied as an insert 2011 (shown in FIG. 21). The insert can include the electronics housing 2001 and a number of flanges 2012a-h extending from the device housing. Any number of flanges 2012a-h may exist, from 0 to N, where N is an integer limited only by the size of the insert. The electronics housing 2001 and/or the flanges can be made of a hard material (e.g., plastic) and/or a flexible material (e.g., silicone, rubber, neoprene, or other flexible material) and configured with a shape or flexible into a shape that conforms to the target dystrophic muscle or muscle group. The insert can be inserted into a device housing 2002 as shown in FIG. 22. The device housing 2002 can be made of a flexible material (e.g., silicone, rubber, neoprene, or other flexible material) and secured around an area of the subject's body that includes the dystrophic muscle or muscle group.

As another example, the light source device 11 can be embodied as a probe device 3011 (FIG. 23). The probe device 3011 can include a device housing 22 that is made of a hard material (e.g., a plastic) and include a portion configured to contact the subject's skin proximal to the dystrophic muscle or muscle group at a 90-degree angle to deliver the light signal. The electronics housing 2001 can be housed within the device housing 2002 with at least the light delivery source clusters 13 being included in an area that contacts the skin. Another example, although not illustrated, can include a flexible array device with a portion shaped to contact the skin at a 180-degree angle to deliver the light signal.

The light source device 11 can include at least one light delivery source to generate the light signal at a certain wavelength, with a certain power, in an operating mode. The operating mode can be at least one of a pulsed operating mode, a continuous operating mode, and a super-pulsed operating mode. The light source device 11 can also include a processing unit 14 programmed (e.g., preprogrammed, programmed in response to an input from the controller 12), which may be in response to an input), or the like) with a time for application of the light signal to the dystrophic muscle or muscle group (e.g., the time can be sufficient to stimulate the phototherapeutic response in the dystrophic muscle or muscle group). The processing unit 14 can also be programmed with the certain wavelength, the certain power, and/or the operating mode. In some instances, the light source device 11 can also include a permanent magnet to provide a static (or constant) magnetic field, which can be used to secure the light source device 11 to the area of the subject's skin and/or to affect the light signal. The constant magnetic field can be from 5 mT to 1 T. Additionally, the light source device 11 can also include a power source. The power source, in some instances, can be an internal battery. In other instances, the power source can receive and/or store power from an external source. In some instances, the external source can be associated with the controller 12.

In some instances, the light signal can include a light wave at a single wavelength of light delivered in a certain operating mode. However, in other instances, the light signal can include a combination of a plurality of individual light waves with different wavelengths of light delivered in two or more different operating modes. The combination of individual light waves is advantageous because the individual light waves can work constructively to create a synergistic effect, enhancing each individual wavelength's ability to penetrate the skin, allowing for a greater portion of the available light energy to reach biological targets beneath the surface of the skin.

The plurality of individual light waves can be generated by a plurality of light delivery sources. Accordingly, the light source device 11 can include a plurality of light delivery sources, each configured to deliver light of a certain wavelength, with a given power, in a pulsed operating mode, a continuous operating mode, or a super-pulsed operating mode. One organization of the plurality of light delivery sources is in one or more light delivery source clusters 13

Figure 2:
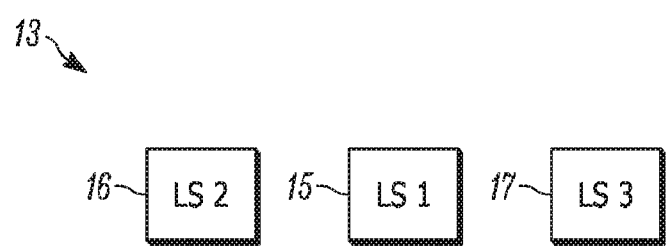
FIG. 2 is a block diagram illustration showing an example configuration of light sources within the light delivery source cluster of FIG. 1.

(an example of an individual cluster is shown in FIG. 2). In practice, the light source device can have any number of light delivery source clusters 13, limited only by the size of the area of the light source device 11 designated for delivery of the light signal.

As shown in FIG. 2, each light delivery source cluster 13 includes three types of light sources (LS1 15, LS2 16, LS3 17). However, the light delivery source clusters 13 may include a greater or fewer number of light sources. Three light sources are shown for simplicity of illustration and explanation. The light sources (LS1 15, LS2 16, LS3 17) each generate light waves with wavelengths within a wavelength range of 600-1100 nm (red to infrared). More particularly, LS1 15 can be configured to generate a first portion of the light signal with a wavelength from 890-910 nm (infrared); LS2 16 can be configured to generate a second portion of the light signal with a wavelength from 600-700 nm (red), and LS3 17 can be configured to generate a third portion of the light signal with a wavelength from 810-880 nm. In this example, LS1 15, which is in the middle of each light delivery source cluster 13, can operate in the super-pulsed operating mode, while LS2 16 and LS3 17, which surround LS1, can each operate in the continuous operating mode or the pulsed operating mode. In other words, LS1 can be a super pulsed laser that creates an impulse of high intensity that emits for a billionth of a second in synchrony with LS2 (a red source, like a red LED or a red light) and/or LS3 (an infrared source, like an infrared LED or an infrared light). Advantageously, the use of the super-pulsed laser (LS1) allows a desired peak power to be delivered for an ultrashort pulse with a minimized level of heat accumulated in the subject's skin and dystrophic muscle or muscle group (in other words, minimizes the photothermal effect).

Many configurations of each light delivery source cluster 13 are possible. Two examples of possible configurations are set forth, but countless other possibilities exist (including with other light sources), as long as there are one or more L1, one or more L2, one or more L3. One possible configuration of each light delivery source cluster 13 is a 1:1:1 configuration, with L1 (the super-pulsed laser) between L2 (the red source) and L3 (the infrared source). Another possible configuration of each light delivery source cluster 13 is a 1:3:3 configuration with L1 surrounded by three (or more) L2 and three (or more) L3. For example, in this configuration, L2 and L3 can alternate as they are arranged around L1 (e.g., L2 L3 L2 L3 L2 L3 surrounding L1). As another example, L2 and L3 can be grouped together around L1 (e.g., L2 L2 L2 L3 L3 L3). Although not expressly described, other example configurations are possible in the 1:3:3 light delivery source cluster 13. The light delivery source clusters 13 within the same light source device 11 can be configured identically, but need not have identical configurations. For example, a light source device 11 can have three light delivery source clusters, with one a 1:1:1 configuration and the other two 1:3:3 configurations.

V. Methods

Another aspect of the present disclosure can include methods 30, 40 (FIGS. 3 and 4) for applying photobiomodulation therapy (PBMT) to a dystrophic muscle or muscle group in a subject who has been diagnosed with a type of dystrophy, like muscular dystrophy. The methods 30, 40 can be executed by hardware—for example, at least a portion of the system 10 shown in FIG. 1 and described above. Additionally, PBMT provides a non-pharmacological therapy to patients suffering from dystrophy, including muscular dystrophy, which can be used alone or in combination with a pharmaceutical treatment (either steroidal or non-steroidal) to manage the symptoms of muscular dystrophy.

The methods 30 and 40 are illustrated as process flow diagrams with flowchart illustrations. For purposes of simplicity, the methods 30 and 40 shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30 and 40. Additionally, one or more elements that implement the methods 30 and 40, such as light source device 11 and/or controller 12 of FIG. 1, may include a non-transitory memory and one or more processors that can facilitate the configuration and generation of the light signal.

Figure 3:
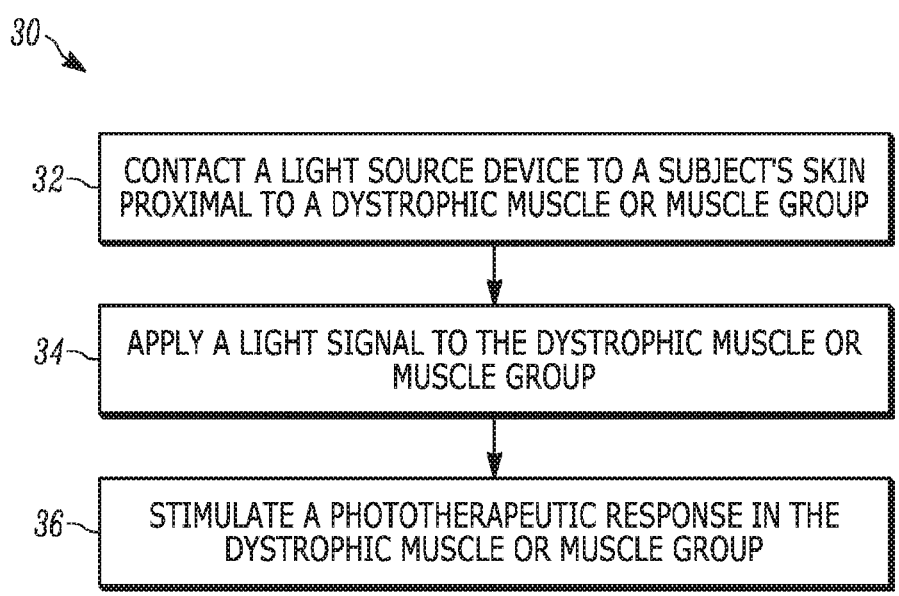
FIG. 3 is a process flow diagram of an example method for applying PBMT to a dystrophic muscle or muscle group to delay dystrophy progression in accordance with another aspect of the present disclosure.

Referring now to FIG. 3, shows a method 30 for applying PBMT to a dystrophic muscle or muscle group to delay dystrophy progression. At step 32, a light source device (e.g. light source device 11) can be contacted to a subject's skin proximal to (e.g., directly adjacent or over) a dystrophic muscle or muscle group. The subject can be any patient who has been diagnosed with any type of dystrophy, including muscular dystrophy.

At step 34, a light signal can be applied to the dystrophic muscle or muscle group. The light signal can be generated in at least one of a pulsed operating mode, a continuous operating mode, and a super-pulsed operating mode. The light signal can include one wave of a single wavelength. However, alternatively, the light signal can include a plurality of individual waves with multiple wavelengths. The combination of the plurality of individual waves can work constructively to create a synergistic effect, enhancing each individual wavelength's ability to penetrate the skin, allowing for a greater portion of the available light energy to reach biological targets beneath the surface of the skin. The light signal is applied for a time sufficient to stimulate a phototherapeutic response in the dystrophic muscle or muscle group. At step 36, a phototherapeutic response can be stimulated in the dystrophic muscle or muscle group. The phototherapeutic response can include modulating gene and/or protein expression of dystrophin. As a result, the progression of muscular dystrophy can be delayed.

Figure 4:
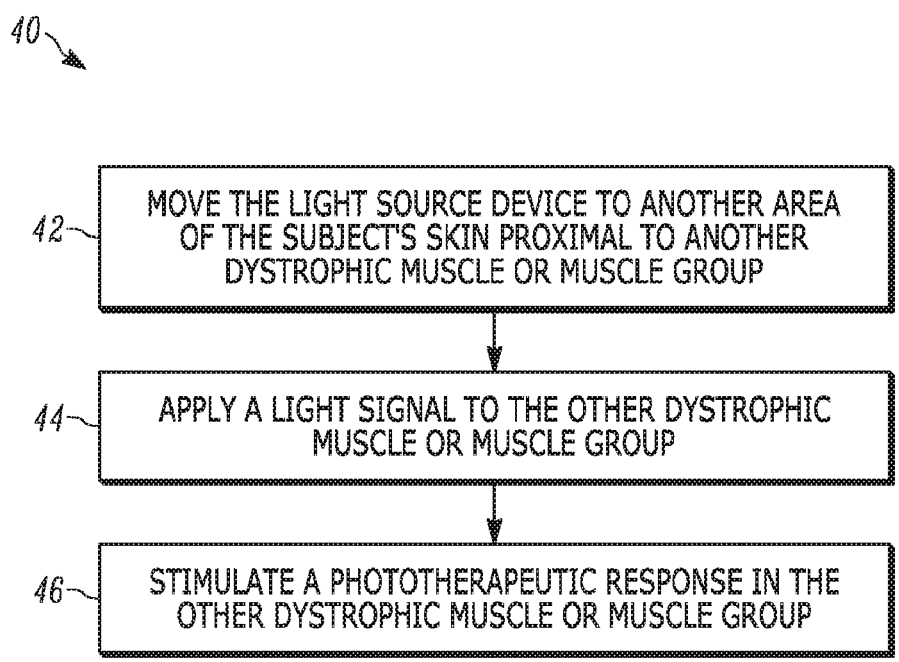
FIG. 4 is a process flow diagram of another example method for applying PBMT to another dystrophic muscle or muscle group to delay dystrophy progression in accordance with a further aspect of the present disclosure.

The method 30 continues in FIG. 4, which shows a method 40 that occurs after moving the light source device. At step 42, the light source (e.g. light source device 11) can be moved to another area of the subject's skin proximal to another dystrophic muscle or muscle group. At step 44, a light signal can be applied to the other dystrophic muscle or muscle group. At step 46, a phototherapeutic response can be stimulated in the other dystrophic muscle or muscle group.

VI. Experimental

The following example is shown for the purpose of illustration only and is not intended to limit the scope of the appended claims.

Experiment 1

This experiment demonstrates the promise of photobiomodulation therapy (PBMT) as a tool for treating Duchene muscular dystrophy (DMD). The PBMT provides a non-pharmacological treatment that does not present harmful side effects, making PBMT a promising tool for treating DMD.

Methods

Animals

All experimental procedures were performed in accordance with the standards of the Brazilian College of Animal Experimentation (COBEA). All experimental protocols were submitted and approved by the Animal Experimentation Ethics Committee of the Universidade Nove de Julho.

The study was conducted in accordance with policies and procedures of Brazilian laws and the United States Department of Health and Human Services.

Experimental Groups

Twenty-five animals were randomly divided into 5 experimental groups with 5 animals in each group:
  Wild Type group—WT mice (C57BL/10ScSn): Untreated
  Placebo-control group—$DMD^{mdx}$ mice: Treated with placebo-control PBMT (using a placebo phototherapy probe).
  1 J PBMT group—$DMD^{mdx}$(mice: Treated with PBMT with doses of 1 J.
  3 J PBMT group—$DMD^{mdx}$(mice: Treated with PBMT with doses of 3 J.
  10 J PBMT group—$DMD^{mdx}$(mice: Treated with PBMT with doses of 10 J.

All treatments started with animals at 6 weeks of age. PBMT was applied bilaterally to a single point on each animal's hindlimb (tibialis anterior muscle) 3 times per week (Monday, Wednesday and Friday) for 14 weeks. The PBMT was delivered by a probe making direct contact with the animal's skin.

Animals were euthanized at 20 weeks of age with an overdose of ketamine and xilazin 24 hours after the last PBMT treatment. After the removal of skin and connective tissue, the tibialis anterior muscles (bilaterally) were removed and processed for further analysis.

Photobiomodulation Therapy Parameters

The probe delivering the PBMT was a cluster probe device with 9 diodes (1 laser diode of 905 nm, 4 LED diodes of 875 nm, and 4 LED diodes of 640 nm manufactured by Multi Radiance Medical™, Solon, Ohio, USA). The parameters used for PBMT are summarized in Table 1. The optical power of the cluster probe device was verified using a power meter (Model S322C, Thorlab®, Newton, N.J., USA) every 2-weeks by a researcher that was not involved in data collection and analysis.

TABLE 1

Parameters for PBMT

| 1 Super-pulsed Infrared Laser Diode | |
| --- | --- |
| Wavelength (nm) | 905 (±1) |
| Frequency (Hz) | 250 |
| Peak Power (W) | 25 |
| Average mean optical output (mW) | 0.625 |
| Power density (mW/cm$^2$) | 1.42 |
| Energy density (J/cm$^2$) | 0.011, 0.0144, or 0.11 |
| Dose (J) | 0.005, 0.0144, or 0.048 |
| Spot size of laser (cm$^2$) | 0.44 |
| 4 Red LEDs | |
| Wavelength (nm) | 640 (±10) |
| Frequency (Hz) | 2 |
| Average optical output (mW) - each | 15 |
| Power density (mW/cm$^2$) - each | 16.66 |
| Energy density (J/cm$^2$) - each | 0.133, 0.383, or 1.283 |
| Dose (J) - each | 0.12, 0.345, or 1.155 |
| Spot size of red LED (cm$^2$) - each | 0.9 |
| 4 Infrared LEDs | |
| Wavelength (nm) | 875 (±10) |
| Frequency (Hz) | 16 |
| Average optical output (mW) - each | 17.5 |
| Power density (mW/cm$^2$) - each | 19.44 |
| Energy density (J/cm$^2$) - each | 0.155, 0.447, or 1.497 |
| Dose (J) - each | 0.14, 0.425, or 1.345 |
| Spot size of infrared LED (cm$^2$) - each | 0.9 |
| Cluster Probe | |
| Magnetic field (mT) | 35 |
| Irradiation time per site (s) | 8, 23, 77 |
| Total dose per site (J) | 1.0, 3.0, or 10.0 |
| Total dose applied in muscular group (J) | 1.0, 3.0, or 10.0 |
| Aperture of device (cm$^2$) | 0.197 |
| Device power density (mW/cm$^2$) | 663.07 |
| Device energy density (J/cm$^2$) | 5.07, 15.23, or 50.76 |
| Application mode | Cluster probe held stationary in skin contact at 90 degree angle and with slight pressure |

Outcomes

Analyses of the PBMT were performed by a blinded researcher.

Analysis Based on Functional Performance Evaluation Protocol

The PBMT was analyzed using a functional performance evaluation protocol. The functional performance evaluation protocol included the animal climbing stairs with the following dimensions (1×0.09 m, distance between the steps of 0.5 cm and)80° using the animal's body weight (the protocol began with the animal's familiarization, in two sessions with a 24-h interval between the sessions). The aim of the sessions was to teach the mouse to move up the steps and consisted of three repetitions to the top, with a 60 s interval to rest. If necessary, a clamp stimulus for the animal to start moving was applied. After this familiarization, the assessments were performed before the treatments begin and 24-h after the last treatment, in order to evaluate how many times each mouse was able to climb up the stairs until the animal came to fatigue. Fatigue was identified when the animal could no longer perform the activity.

Analysis Based on Morphological Assessment

The tibialis anterior muscles of the animal's hind paw were collected and stored in 10% buffered formalin for histological processing; then, hematoxylin and eosin staining was performed in a routine method. Slides were photographed, and the morphology of the skeletal striated muscle fibers was analyzed (Eclipse E-200; Nikon, Tokyo, Japan). Images of all groups were obtained using the 400 × magnification. The images were presented with a similar photographic pattern.

Analysis Based on RNA Isolation and Real-Time Polymerase Chain Reaction (RT-PCR)

Muscles were thawed, and Trizol was immediately added (Gibco BRL, Life Technologies, Rockville, Md., USA, 1 ml/100 mg tissue). Then, muscles were homogenized for the recovery of total RNA, according to the manufacturer's instruction. DNase I was employed to digest DNA to obtain RNA purification and the integrity of RNA was verified by agarose gel electrophoresis. Total RNA (2 mg) was used for first-strand cDNA synthesis [reverse transcriptase (RT)] using SuperScript II. RNaseOUT was also added to protect the RNA during this process. Three pooled RNA aliquots were routinely sham reverse transcribed (i.e., reverse transcriptase omitted) to ensure the absence of DNA contaminants.

Diluted RT samples (1:10) were submitted to real-time PCR amplification using Platinum Sybr QPCR Supermix- UDG and specific oligonucleotides (designed using http://www.ncbi.nlm.nih.gov/tools/primer-blast/). The primer used was dystrophin anti-sense: AGGTCTAG-GAGGCGTTTTCC was used as an internal control b-actin sense: GGCTGTATTCCCCTCCATCG; b-actin anti-sense: CCAGTTGGTAACAATGCCAT GT. The conditions for PCR were as follows: 50 µC–2 min; 95 µC–2 min, followed by 30 cycles of 95 µC–15 s; 60 µC–1 min, followed by 72 µC–15 s. Cycle threshold (Ct) values were recorded for each gene, and the results of genes of interest were normalized to results obtained with the internal control gene. Delta-Delta-Ct (ddCt) values were calculated and results expressed as fold increases. All oligonucleotides and reagents utilized were purchased from Invitrogen (Thermo Fisher Scientific, Waltham, Mass., USA).

Analysis Based on Western Blotting

Frozen samples of tibialis anterior muscles were homogenized using ice-cold lysis buffer and proteinase inhibitor cocktail. Lysates corresponding to 30 µg of protein were subjected to 10% SDS-PAGE. Separated proteins were transferred to PVDF membrane (Amersham Biosciences, N.J., USA), and transfer effectiveness was examined with 0.5 ?/o Ponceau S. After blocking with 5% non-fat dry milk for 2 h at room temperature, PVDF membranes were probed with Abcam (Cambridge, Mass., USA) primary antibodies for rabbit anti-dystrophin (1:5000) in overnight incubation. Membranes were then washed five times with PBS and incubated for 1 h with horseradish peroxidase-conjugated anti-rabbit (1:20,000; Zymed, Calif., USA). Membranes were again washed five times with blocking buffer and then rinsed twice with PBS. Antibodies binding were detected by chemiluminescence reagents (Amersham Biosciences, N.J., USA), and images were captured using an Amersham Imager 600 system. Quantification of target proteins was normalized for the internal control glyceraldehyde 3-phosphate dehydrogenase.

Statistical Analysis

The Kolmogorov-Smirnov test was used to verify the normal distribution of data. A non-paired t test was used to verify statistical significance between WT and placebo-control groups regarding gene and protein expression of dystrophin. A one-way ANOVA test followed by a Bonferroni post-hoc test was performed to verify statistical significance between multiple groups regarding gene and protein expression of dystrophin. For the functional analysis, the two-way ANOVA test followed by the Bonferroni post-hoc test was performed to verify statistical significance among groups. The level of statistical significance was set at $p<0.05$. Data analyses were performed using the mean values and standard deviation (SD). However, in graphs, data are presented as mean and standard error of the mean (SEM).

Results

The following results demonstrate the effects of PBMT, at different treatment doses, in an experimental model of DMD.

Functional Assessment

Figure 5:
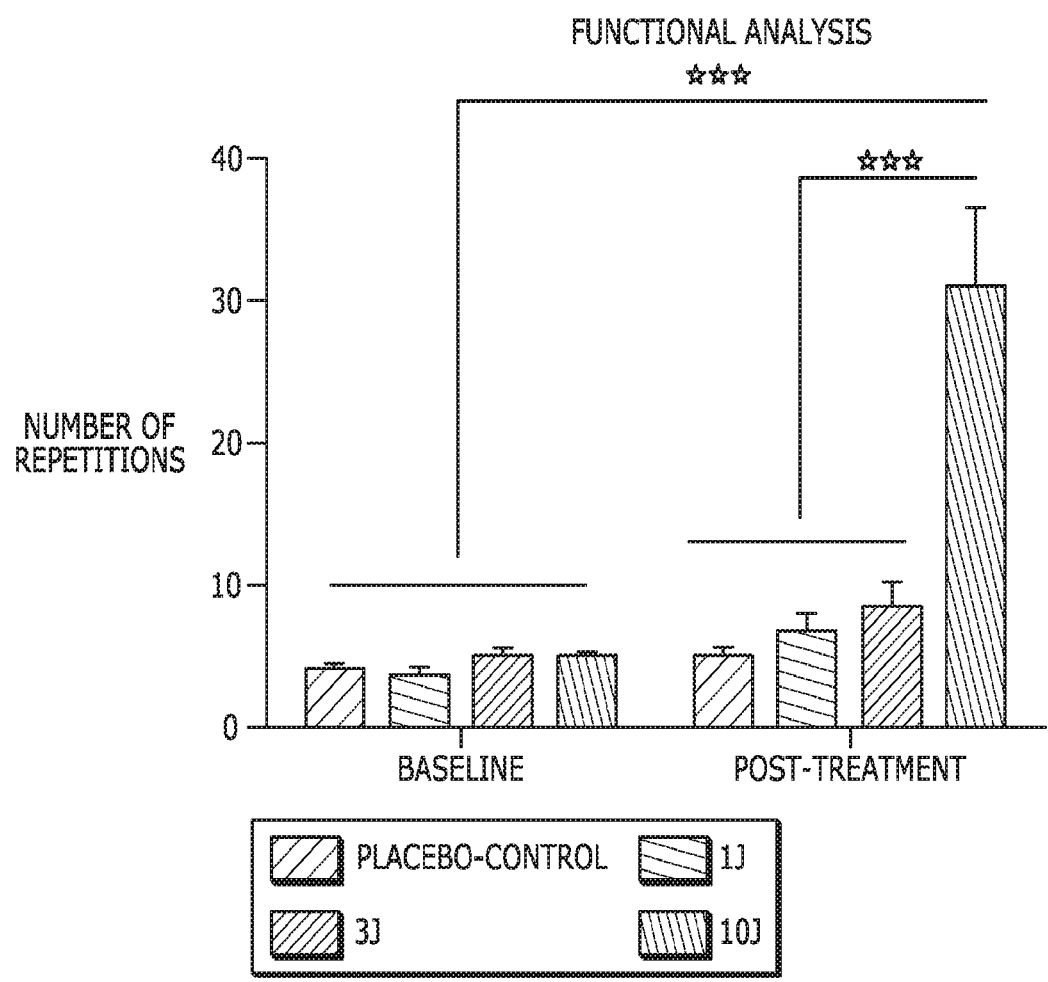
FIG. 5 shows a functional performance assessment of subjects treated with PBMT compared a control group.

All the treatment groups, as well as the placebo-control group, had the same mean number of repetitions when subjected to the ascending ladder test before treatments begin. Therefore, the groups were homogeneous prior to treatment, indicating that meaningful comparisons could be made. In the post-treatment evaluation, the 10 J group showed a significantly increased number of repetitions, both when compared to the placebo-control group and to the other treatment groups, as shown in FIG. 5.

Morphological Analysis

Figure 6:
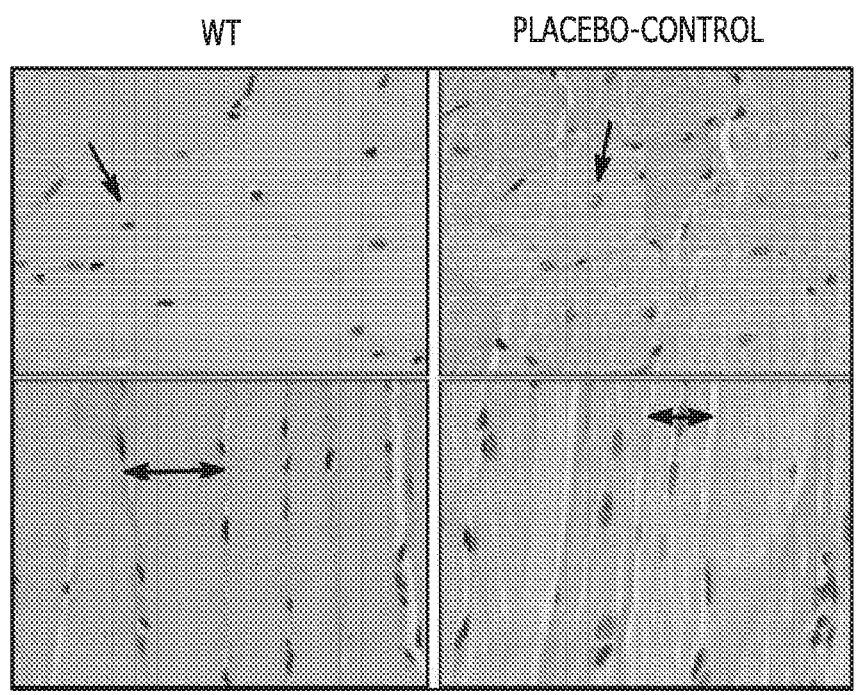
FIG. 6 shows photomicrographs of histological muscle sections (longitudinal and transversal sections) of wild type (WT) and placebo-control groups (HE, original magnification ×400)

Compared to wild-type mice (WT), the placebo-control group presented a marked amount of connective tissue, as shown in FIG. 6, with a decrease in the number and size of muscle fibers, less positioning of the nuclei at the center of the muscle fibers and fewer nuclear clusters. All of which indicate degeneration of the muscle tissue.

Figure 7:
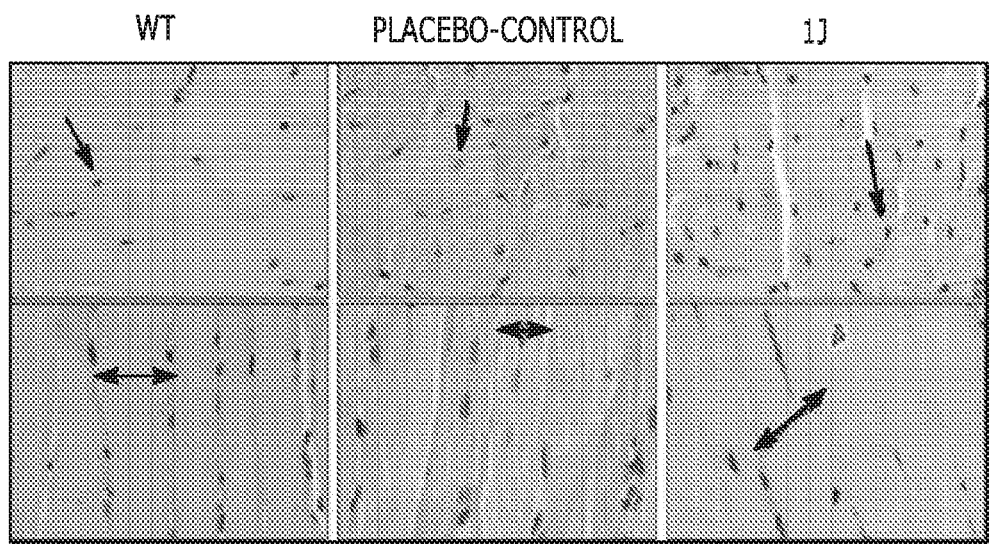
FIG. 7 shows photomicrographs of histological muscle sections (longitudinal and transversal sections) of wild type (WT), placebo-control, and 1 J groups (HE, original magnification ×400)
Figure 8:
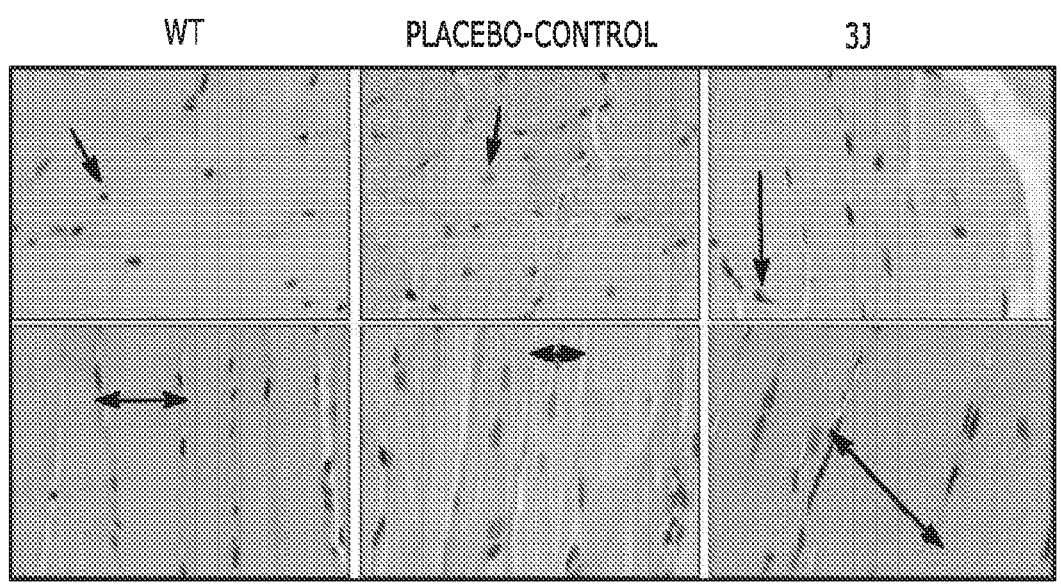
FIG. 8 shows photomicrographs of histological muscle sections (longitudinal and transversal sections) of wild type (WT), placebo-control, and 3 J groups (HE, original magnification ×400)
Figure 9:
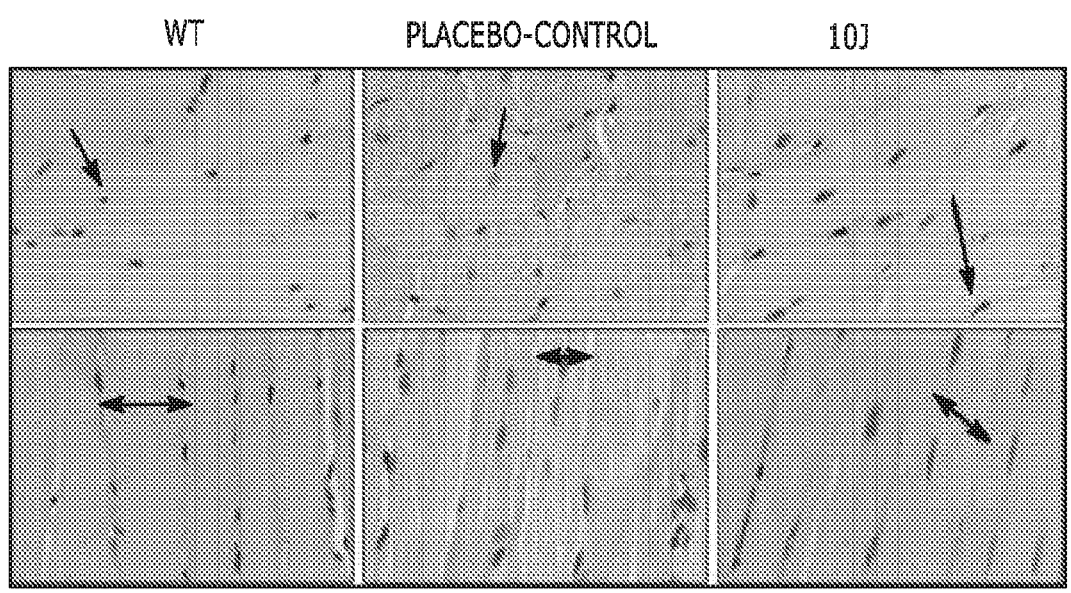
FIG. 9 shows photomicrographs of histological muscle sections (longitudinal and transversal sections) of wild type (WT), placebo-control, and 10 J groups (HE, original magnification ×400)

A histological comparison of the WT and placebo-control groups revealed that dystrophin-deficient $DMD^{mdx}$ mice (placebo-control group) showed a reduction in the number of fibers and an expressive reduction in volume, indicating that the myofibers are persistently immature. The nuclei were grouped and centrally located, indicating attempted regeneration to counteract the degenerative process. However, compared to the placebo-control group, the groups treated with PBMT showed signs of improvement, though these changes were dose-dependent (FIGS. 7, 8, and 9). Compared to the placebo-control group, 1 J group did not present marked morphological differences (FIG. 7). The 3 J group had practically no nuclei displaced to the center and no nuclear grouping, as shown in FIG. 8. This indicates a delay in the pathological progression of the disease. Compared to the control, 10 J group showed some minimization of the morphopathological aspects of the disease (FIG. 9). However, this decrease was slightly lower than observed in 3 J group.

Gene Expression Analysis

Figure 10:
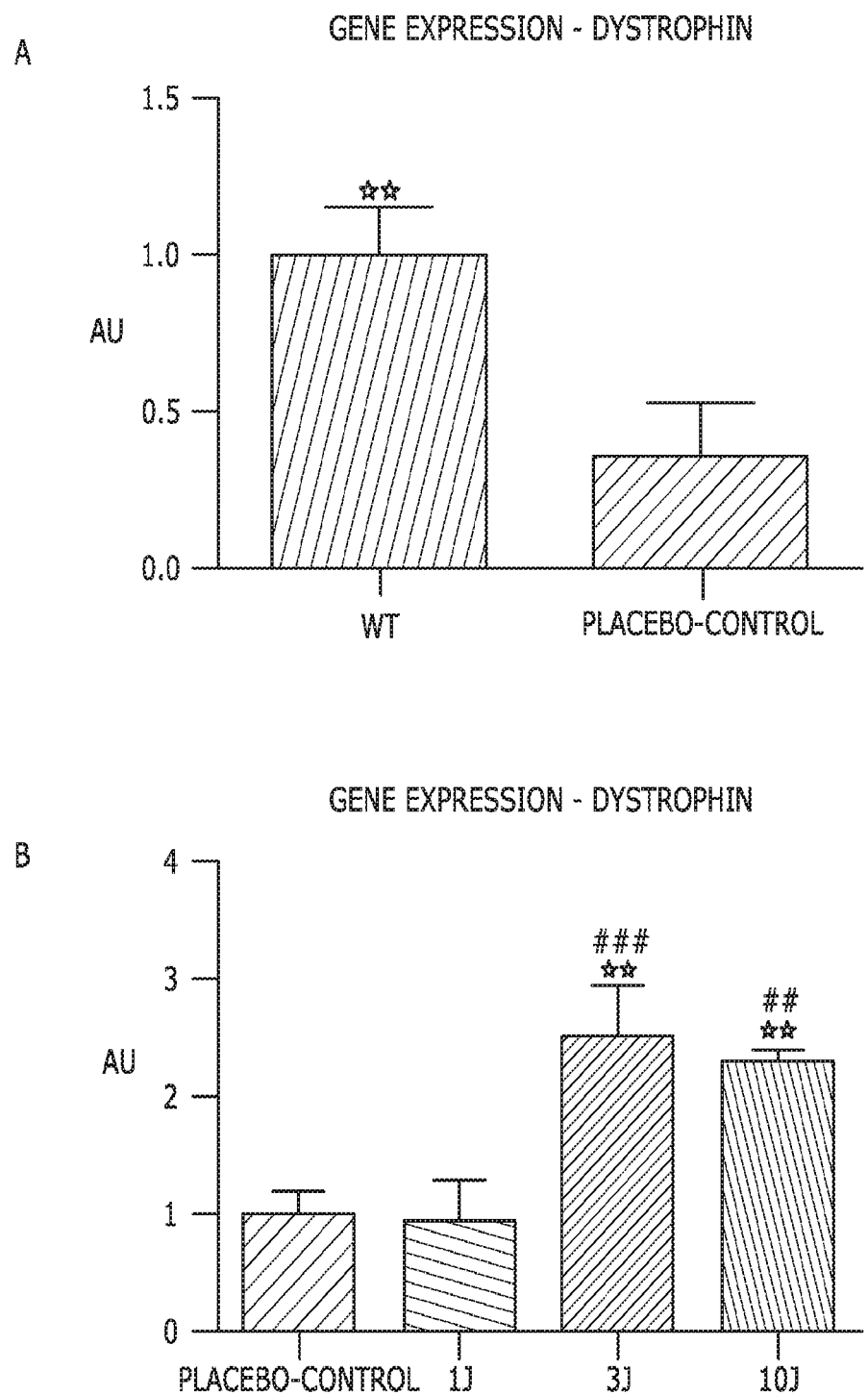
FIG. 10 shows the mRNA gene expression of dystrophin in (a) WT compared to placebo-control groups and (b) placebo-control, 1 J, 3 J, and 10 J groups.

Dystrophin gene expression was significantly reduced in the placebo-control group compared to the WT group ($p<0,01$), as presented in FIG. 10a. The 1 J group showed no significant difference when compared to the placebo-control group. The 3 J ($p<0.01$) and 10 J groups ($p<0.01$) showed statistically significant increases in dystrophin gene expression compared to placebo-control group as presented in FIG. 10b.

Protein Expression Analysis

Figure 11:
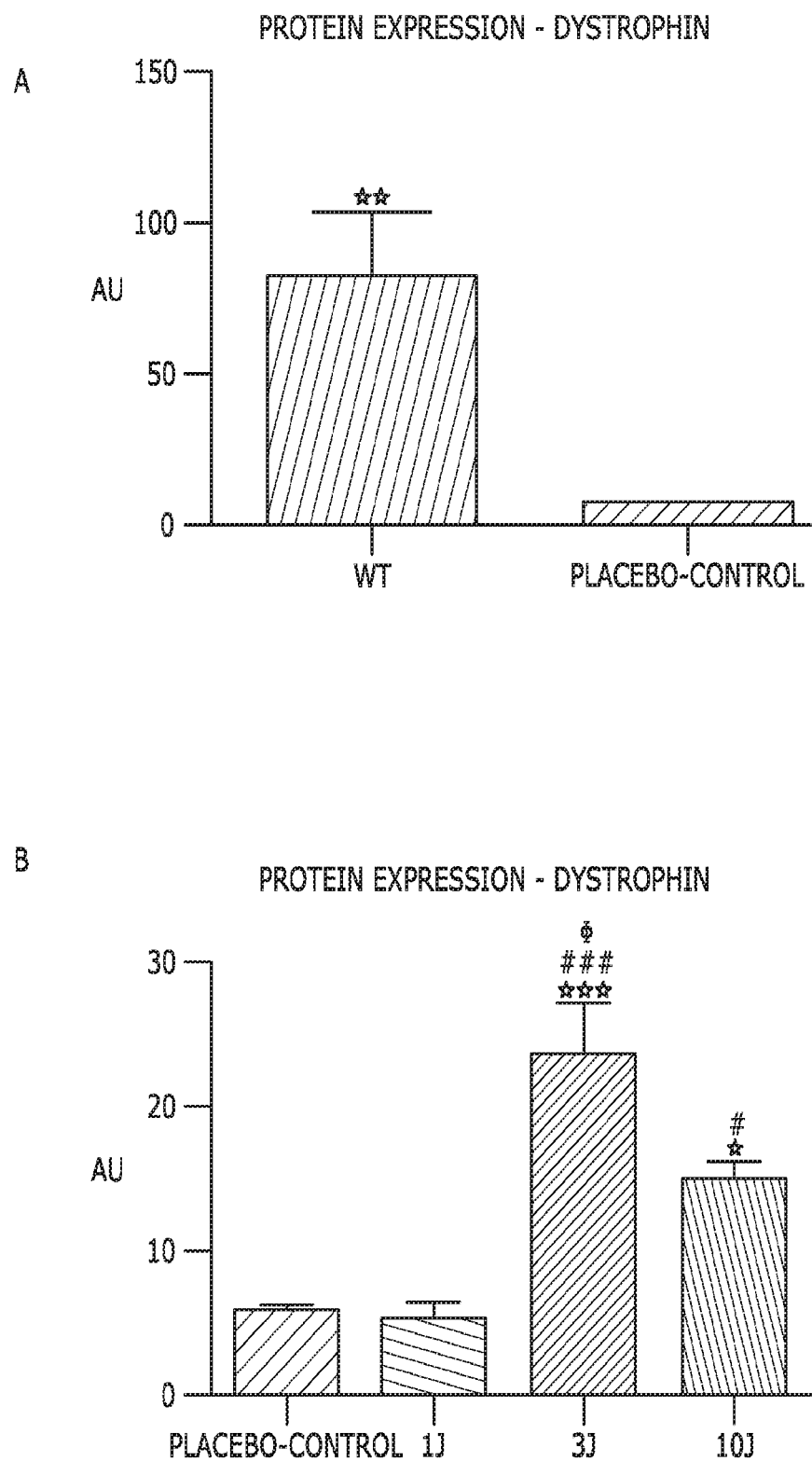
FIG. 11 shows the protein expression of dystrophin in (a) WT compared to placebo-control groups and (b) placebo-control, 1 J, 3 J, and 10 J groups.

The same pattern was found for dystrophin protein expression analysis, in which the placebo-control group showed significant difference from the WT group ($p<0.01$), as presented in FIG. 11a. The comparison between all treated groups showed that the 1 J group had no difference from the placebo control group; however, the 3 J ($p<0.001$) and 10 J groups ($p<0.05$) presented an increase in dystrophin protein expression compared to placebo-control group, as shown in FIG. 11b.

Experiment 2

This experiment compares the effects of photobiomodulation therapy (PBMT), non-steroidal anti-inflammatory drugs (NSAID), and glucocorticoids as isolated and combined treatments on dystrophin, skeletal muscle tissue morphology, and functional performance in mdx mice. It is shown that PBMT can preserve muscle morphology and improve muscular function of mdx mice through modulation of dystrophin.

Methods

Mice were randomly divided into 7 different experimental groups: Wild Type (WT), Placebo-control (mdx mice), Prednisone (mdx mice), NSAID (mdx mice), PBMT prednisone (mdx mice), and PBMT+NSAID (mdx mice). Prednisone (glucocorticoid) treatment was administered to animals daily with a dose of 1.5 mg/kg per day; NSAID treatment with ibuprofen was also administered to animals daily with a dose of 25 mg/kg per day. PBMT was performed employing a cluster probe (Multi Radiance Medical, Solon, Ohio) with 9 diodes (1 super-pulsed laser diode (905 nm), four LED diodes (875 nm), and 4 LED diodes (650 nm). PBMT was applied 3 times a week with direct contact to the animal's skin on hindlimb at a single point (tibialis anterior muscle—bilaterally). For combined treatments, each modality was applied as described previously. All treatments were performed during 14 weeks and started with animals at 6 weeks of age. The analysis consisted of muscle morphology, dystrophin through itntnunohistochetnistry and functional performance.

Results

Figure 12:
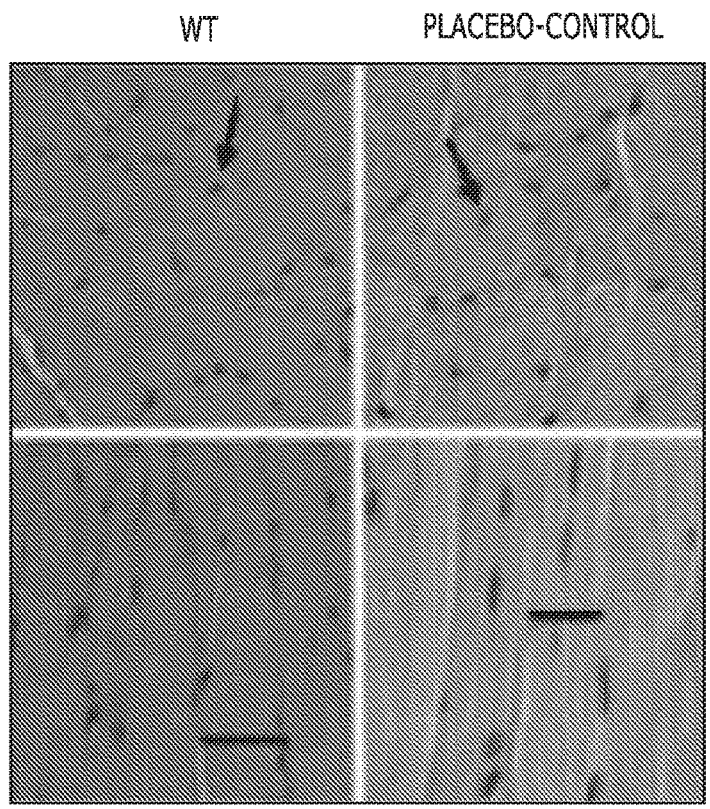
FIG. 12 shows photomicrographs of histological muscle sections (longitudinal and transversal sections) of wild type (WT) and placebo-control groups (HE, original magnification ×400)
Figure 13:
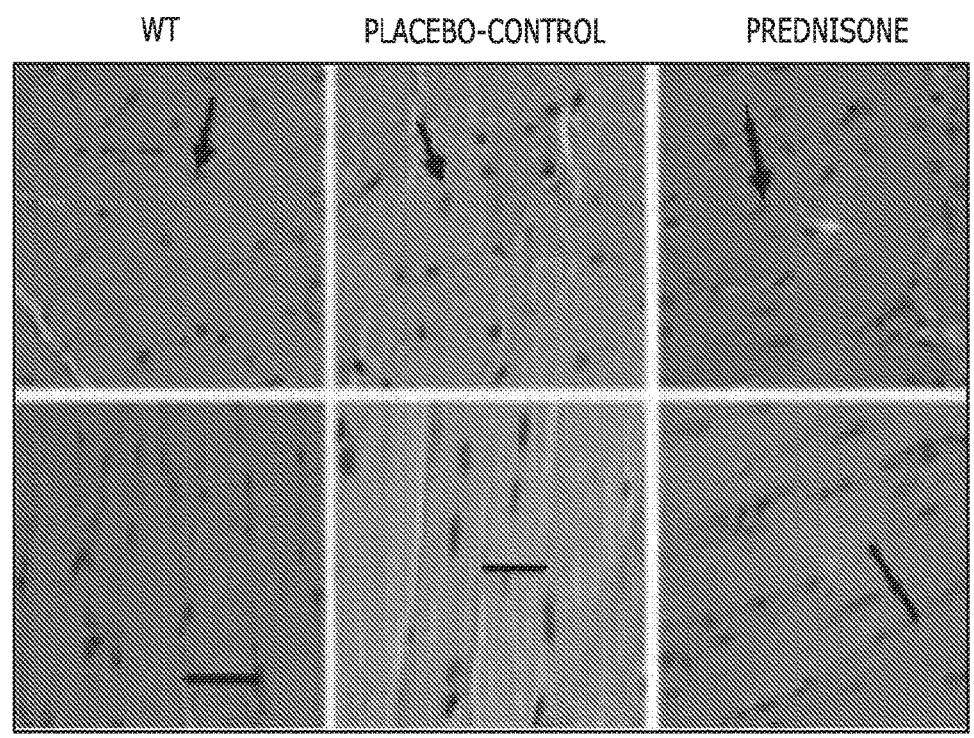
FIG. 13 shows photomicrographs of histological muscle sections (longitudinal and transversal sections) of wild type (WT) and Prednisone groups (HE, original magnification ×400)
Figure 14:
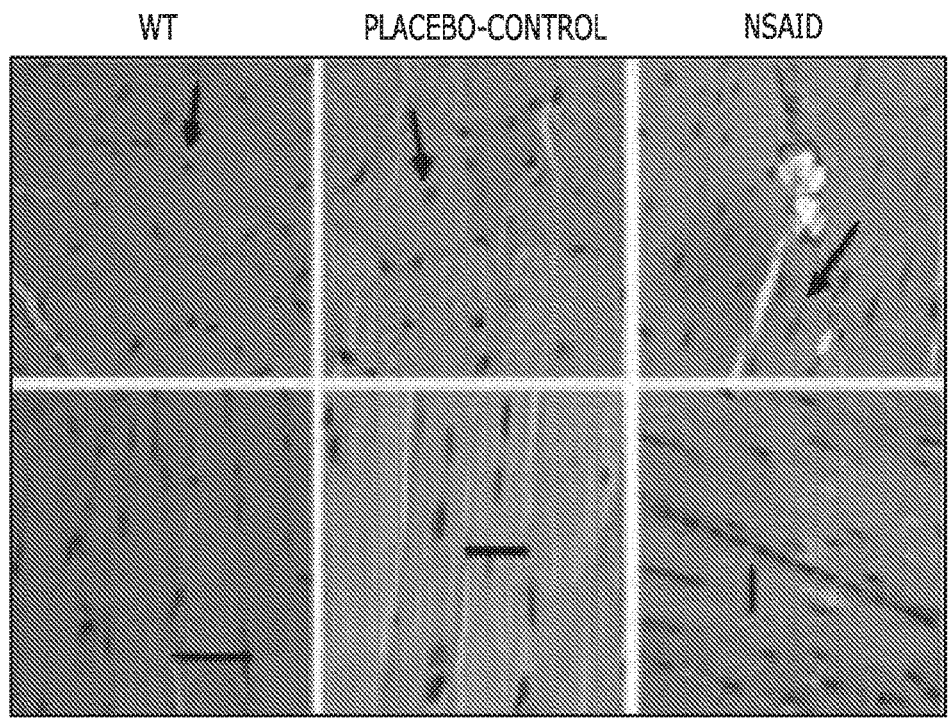
FIG. 14 shows photomicrographs of histological muscle sections (longitudinal and transversal sections) of wild type (WT) and NSAID groups (HE, original magnification ×400)
Figure 15:
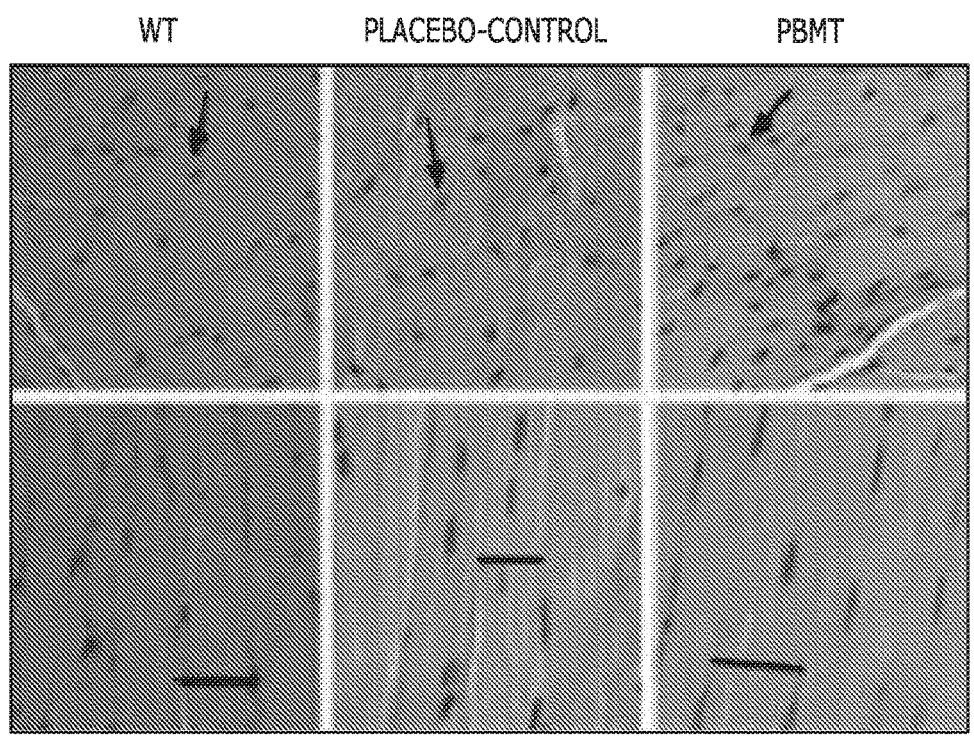
FIG. 15 shows photomicrographs of histological muscle sections (longitudinal and transversal sections) of wild type (WT) and PBMT groups (HE, original magnification ×400)
Figure 16:
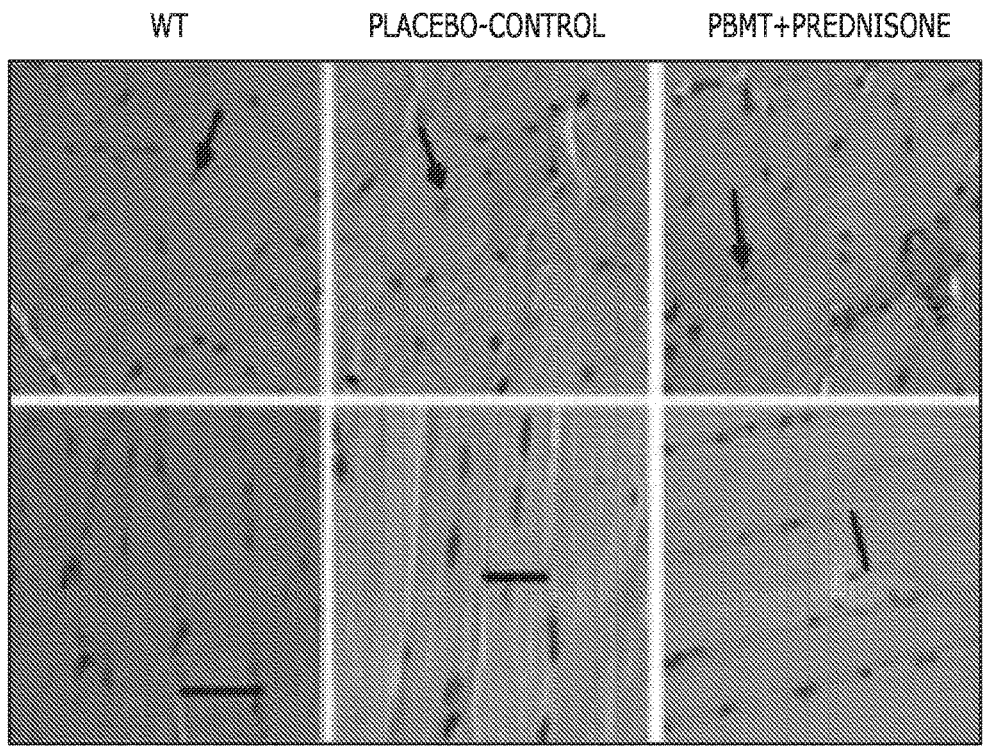
FIG. 16 shows photomicrographs of histological muscle sections (longitudinal and transversal sections) of wild type (WT) and PBMT+Prednisone groups (HE, original magnification ×400)
Figure 17:
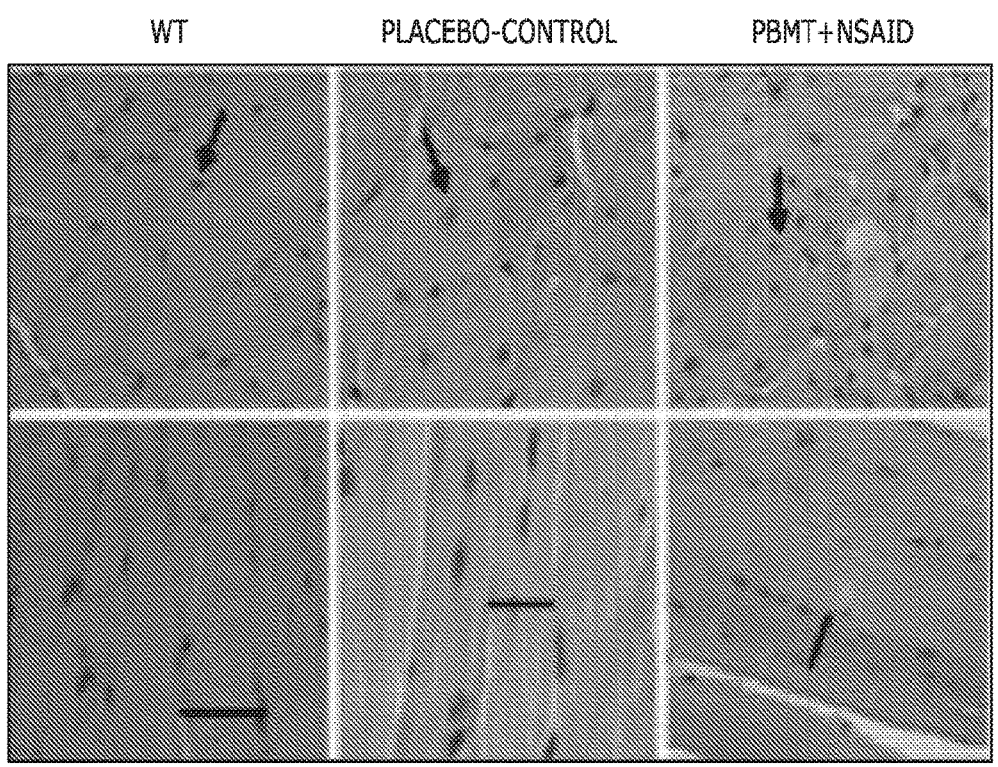
FIG. 17 shows photomicrographs of histological muscle sections (longitudinal and transversal sections) of wild type (WT) and PBMT+NSAID groups (HE, original magnification ×400)
Figure 18:
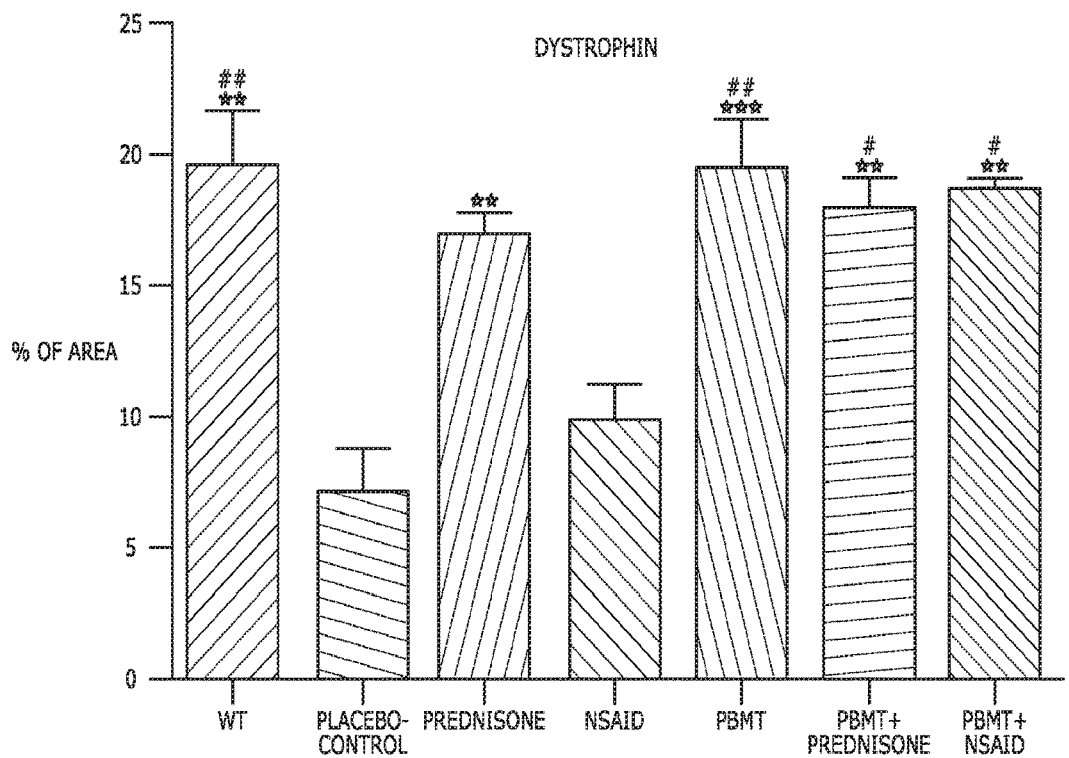
FIG. 18 shows the protein expression of dystrophin in each group.
Figure 19:
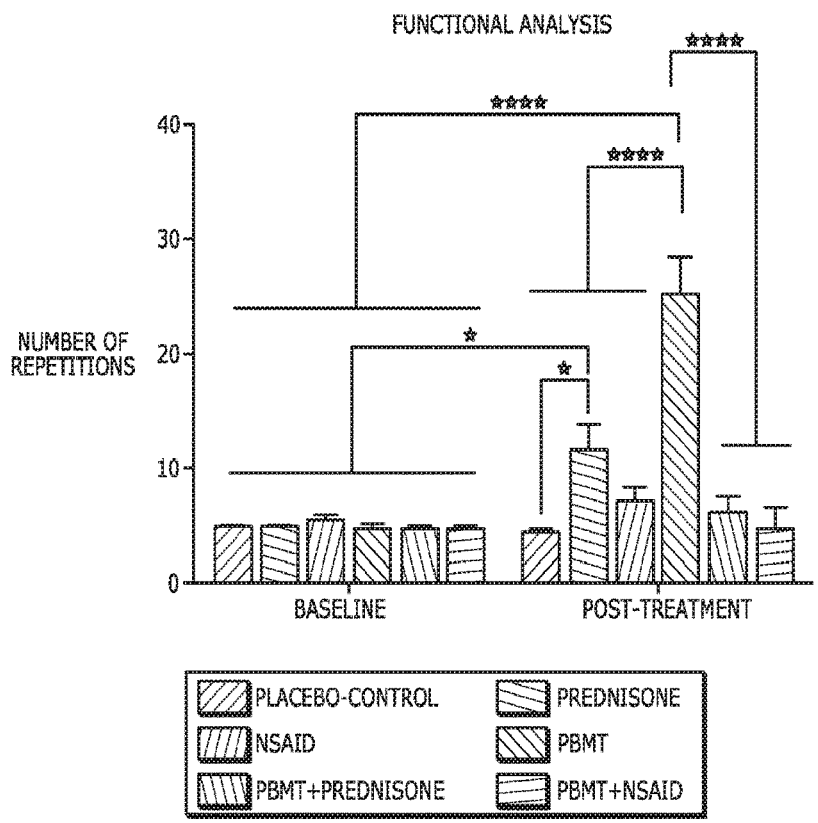
FIG. 19 shows a functional performance assessment comparing subjects of each group.

The Prednisone group (FIG. 13), PBMT group (FIG. 15), PBMT Prednisone group (FIG. 16), and PBMT+NSAID group (FIG. 17) showed an increased dystrophin compared to the placebo-control group (FIG. 18); the Placebo-control group (FIG. 12) and the NSAID group (FIG. 14) showed no significant increase in dystrophin compared to the placebo-control group. The Prednisone group, PBMT group, PBMT Prednisone group, and PBMT+NSAID group also lead to an improvement in the morphological aspects of skeletal muscle in a similar way. Only Prednisone and PBMT treatments lead to improved muscular function in mice compared to the placebo-control group (FIG. 19). PBMT treatment presented the best outcomes for functional performance compared to all other groups.

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

The following is claimed:

1. A method comprising:
   contacting a light source device to a subject's skin proximal to a dystrophic muscle or muscle group, wherein the subject has been diagnosed with muscular dystrophy; and
   applying a light signal through the light source device to the dystrophic muscle or muscle group,
   wherein the light source device comprises at least three light sources comprising at least a first light source operating in a super-pulsed operating mode and configured to generate a first portion of the light signal with a wavelength from 890-910 nm, a second light source operating in a pulsed operating mode or a continuous operating mode and configured to generate a second portion of the light signal with a wavelength from 600-700 nm, and a third light source operating in the pulsed operating mode or the continuous operating mode and configured to generate a third portion of the light signal with a wavelength from 810-880 nm,
   wherein the first light source comprises a super pulsed laser that creates an impulse of high intensity that emits for a billionth of a second in synchrony with a portion of the third light signal generated by the third light source.

2. The method of claim 1, wherein the light source device is a probe device or a flexible array device.

3. The method of claim 1, wherein the light signal causes a modulation of gene and/or protein expression of dystrophin.

4. The method of claim 1, wherein the first light source comprises a super-pulsed infrared laser source, the second light source comprises a red light source, and the third light source comprises an infrared light source.

5. The method of claim 4, wherein the second light source further comprises at least three red light sources and the third light source further comprises at least three infrared light sources.

6. The method of claim 4, wherein the light source device further comprises a permanent magnet that provides a constant magnetic field.

7. The method of claim 6, wherein the constant magnetic field has a magnetic induction from 5 mT to 1 T.

8. The method of claim 1, further comprising:
   moving the light source device to another area of the subject's skin proximal to another dystrophic muscle or muscle group; and
   applying the light signal through the light source device to the other dystrophic muscle or muscle group.

9. The method of claim 8, wherein the light source device is a portable device that receives power from an internal power source or an external power source.

10. The method of claim 8, wherein the light source device is removably secured to the area of the subject's skin and the other area of the subject's skin.

11. A light source device configured to contact a subject's skin proximal to a dystrophic muscle or muscle group comprising:
    a cluster of light delivery sources comprising:
       a first light source comprising a super pulsed laser configured to generate a first portion of a light signal with a wavelength from 890-910 nm in a super-pulsed operating mode;
       a second light source configured to generate a second portion of the light signal with a wavelength from 600-700 nm in a pulsed operating mode or a continuous operating mode; and
       a third light source configured to generate a third portion of the light signal with a wavelength from 810-880 nm in the pulsed operating mode or the continuous operating mode, wherein the first light source creates an impulse of high intensity that emits for a billionth of a second in synchrony with a part of the third portion of the light signal generated by the third light source;
    a permanent magnet that provides a constant magnetic field having a magnetic induction from 5 mT to 1 T;
    a processing unit preprogrammed with a time for application of the light signal to the dystrophic muscle or muscle group; and
    a power source.

12. The light source device of claim 11, wherein the first light source comprises a super-pulsed infrared laser source, the second light source comprises at least two red light sources, and the third light source comprises at least two infrared light sources.

13. The light source device of claim 12, wherein the at least two red light sources comprise red light emitting diodes and the at least two infrared light sources comprise infrared light emitting diodes.

14. The light source device of claim 11, further comprising a securing mechanism to removably secure the light source device to the area of the subject's skin.

* * * * *